United States Patent
Yan et al.

(10) Patent No.: US 12,376,763 B2
(45) Date of Patent: Aug. 5, 2025

(54) NON-CONTACT RESPIRATION SENSING

(71) Applicant: Apple Inc., Cupertino, CA (US)

(72) Inventors: Miaolei Yan, Santa Clara, CA (US);
Tong Chen, Fremont, CA (US);
Nicholas C. Soldner, Los Altos, CA (US)

(73) Assignee: Apple Inc., Cupertino, CA (US)

( * ) Notice: Subject to any disclaimer, the term of this patent is extended or adjusted under 35 U.S.C. 154(b) by 97 days.

(21) Appl. No.: 18/202,140

(22) Filed: May 25, 2023

(65) Prior Publication Data

US 2024/0000341 A1    Jan. 4, 2024

Related U.S. Application Data

(60) Provisional application No. 63/402,597, filed on Aug. 31, 2022, provisional application No. 63/356,955, filed on Jun. 29, 2022.

(51) Int. Cl.
*A61B 5/087*    (2006.01)
*A61B 5/00*    (2006.01)

(52) U.S. Cl.
CPC .......... *A61B 5/0873* (2013.01); *A61B 5/0082* (2013.01); *A61B 5/6803* (2013.01)

(58) Field of Classification Search
CPC .... A61B 5/0873; A61B 5/0082; A61B 5/6803
See application file for complete search history.

(56) References Cited

U.S. PATENT DOCUMENTS

| | | | |
|---|---|---|---|
| 4,402,601 A | 9/1983 | Riva | |
| 4,657,382 A | 4/1987 | Busujima et al. | |
| 5,063,938 A * | 11/1991 | Beck | A61B 5/0816 128/200.26 |
| 5,450,193 A * | 9/1995 | Carlsen | G01J 3/44 356/246 |
| 5,748,295 A | 5/1998 | Farmer | |
| 5,786,893 A * | 7/1998 | Fink | G01J 3/44 359/885 |
| 5,825,465 A | 10/1998 | Nerin et al. | |
| 5,895,922 A * | 4/1999 | Ho | G01N 21/64 250/492.1 |

(Continued)

FOREIGN PATENT DOCUMENTS

| | | |
|---|---|---|
| CN | 2163384 | 4/1994 |
| CN | 1279394 | 1/2001 |

(Continued)

OTHER PUBLICATIONS

Donati [Self-Mixing Interferometer With a Laser Diode: Unveiling the FM Channel and Its Advantages Respect to the AM Channel, IEEE Journal of Quantum Electronics, vol. 53, No. 5, Oct. 2017]. (Year: 2017).*

(Continued)

*Primary Examiner* — Oommen Jacob
(74) *Attorney, Agent, or Firm* — Brownstein Hyatt Farber Schreck, LLP

(57) ABSTRACT

A head mounted device may include one or more interferometric sensors positioned and oriented in a housing to sense particle movement caused by respiration of a user. Interferometric signals from the one or more interferometric sensors may be used to determine respiration information about the user.

18 Claims, 16 Drawing Sheets

(56) References Cited

U.S. PATENT DOCUMENTS

| | | | |
|---|---|---|---|
| 6,185,446 B1* | 2/2001 | Carlsen, Jr. | A61B 5/055 600/529 |
| 6,233,045 B1 | 5/2001 | Suni et al. | |
| 6,794,671 B2 | 9/2004 | Nicoli et al. | |
| 7,227,180 B2 | 10/2007 | Townley-Smith et al. | |
| 7,384,793 B2* | 6/2008 | McCash | G01N 33/5695 435/286.2 |
| 7,388,672 B2 | 6/2008 | Zhou et al. | |
| 7,619,744 B2 | 11/2009 | Liess | |
| 7,990,521 B2 | 8/2011 | Ueno | |
| 7,995,193 B2 | 8/2011 | Kuwata | |
| 8,047,055 B2* | 11/2011 | Wang | G01N 15/0205 250/397 |
| 8,339,584 B2 | 12/2012 | Christian et al. | |
| 8,416,424 B2 | 4/2013 | Werner et al. | |
| 8,477,311 B2* | 7/2013 | Russell | G01J 3/02 356/417 |
| 8,532,751 B2 | 9/2013 | McKenna | |
| 8,625,099 B2 | 1/2014 | Sakamoto et al. | |
| 8,820,147 B2 | 9/2014 | Sinha | |
| 8,982,336 B2 | 3/2015 | Ueno | |
| 9,229,024 B2 | 1/2016 | Carpaij et al. | |
| 9,354,315 B2 | 5/2016 | Lepaysan et al. | |
| 9,397,476 B2 | 7/2016 | Baier et al. | |
| 9,726,474 B2 | 8/2017 | Royo Royo et al. | |
| 9,759,736 B2 | 9/2017 | Zamama et al. | |
| 9,778,177 B2 | 10/2017 | Roke et al. | |
| 10,180,397 B2 | 1/2019 | Rakic et al. | |
| 10,379,028 B2 | 8/2019 | Spruit et al. | |
| 10,390,730 B1 | 8/2019 | Shoeb | |
| 10,503,048 B2 | 12/2019 | Del Bino et al. | |
| 10,788,308 B2* | 9/2020 | Mutlu | G01B 9/02017 |
| 11,054,244 B2 | 7/2021 | Ouweltjes et al. | |
| 11,112,235 B2 | 9/2021 | Mutlu et al. | |
| 11,119,021 B2 | 9/2021 | Spruit et al. | |
| 11,187,643 B2 | 11/2021 | Jutte et al. | |
| 11,243,068 B1 | 2/2022 | Mutlu et al. | |
| 11,409,365 B2 | 8/2022 | Mutlu et al. | |
| 11,419,546 B2 | 8/2022 | Cihan et al. | |
| 11,428,819 B2 | 8/2022 | Spruit et al. | |
| 11,450,293 B2 | 10/2022 | Chen et al. | |
| 11,473,898 B2 | 10/2022 | Mutlu et al. | |
| 2004/0015092 A1* | 1/2004 | Pettersson | A61M 16/0666 604/94.01 |
| 2008/0231857 A1* | 9/2008 | Depeursinge | A61B 5/14552 356/246 |
| 2009/0259114 A1* | 10/2009 | Johnson | A61B 5/14553 600/310 |
| 2011/0028802 A1* | 2/2011 | Addison | A61B 5/08 600/323 |
| 2012/0002189 A1 | 1/2012 | Bengoechea Apezteguia et al. | |
| 2012/0050044 A1* | 3/2012 | Border | A61M 21/02 340/573.1 |
| 2013/0010288 A1* | 1/2013 | Dwyer | A62B 23/02 356/213 |
| 2013/0276785 A1* | 10/2013 | Melker | A61M 16/0677 128/204.23 |
| 2014/0275857 A1* | 9/2014 | Toth | A61M 16/085 600/301 |
| 2015/0148636 A1* | 5/2015 | Benaron | A61B 5/02405 600/328 |
| 2015/0265161 A1* | 9/2015 | Hernandez | A61B 5/0816 600/483 |
| 2017/0281051 A1* | 10/2017 | Evans | A61M 16/06 |
| 2018/0081179 A1* | 3/2018 | Samec | G01J 3/10 |
| 2018/0092589 A1* | 4/2018 | Tzvieli | A61B 5/7267 |
| 2018/0206737 A1* | 7/2018 | Colman | A61B 5/6838 |
| 2018/0328841 A1* | 11/2018 | Graham | A61B 5/0816 |
| 2019/0285537 A1 | 9/2019 | Spruit et al. | |
| 2020/0064249 A1* | 2/2020 | Momtahan | G01N 15/0211 |
| 2020/0072723 A1 | 3/2020 | Weiss et al. | |
| 2020/0096310 A1* | 3/2020 | Mutlu | G01B 9/02017 |
| 2020/0138292 A1* | 5/2020 | Choi | A61B 5/091 |
| 2020/0319082 A1 | 10/2020 | Mutlu et al. | |
| 2020/0337631 A1 | 10/2020 | Sahin | |
| 2020/0350744 A1 | 11/2020 | Gertach | |
| 2021/0010797 A1 | 1/2021 | Cihan et al. | |
| 2021/0080248 A1 | 3/2021 | Cihan et al. | |
| 2021/0302745 A1 | 9/2021 | Mutlu et al. | |
| 2021/0364273 A1 | 11/2021 | Mutlu et al. | |
| 2022/0099431 A1 | 3/2022 | Chen et al. | |
| 2022/0218293 A1* | 7/2022 | Chou | A61B 7/003 |
| 2024/0000337 A1* | 1/2024 | Chen | A61B 5/113 |
| 2024/0000341 A1* | 1/2024 | Yan | A61B 5/0873 |

FOREIGN PATENT DOCUMENTS

| | | |
|---|---|---|
| CN | 1682105 | 10/2005 |
| CN | 102564909 | 7/2012 |
| CN | 103733061 | 4/2014 |
| CN | 106226783 | 12/2016 |
| CN | 207231962 | 4/2018 |
| CN | 109154659 | 1/2019 |
| CN | 108692663 | 4/2020 |
| DE | 102016210830 | 12/2017 |
| EP | 3514898 | 7/2019 |
| JP | H06331745 | 12/1994 |
| WO | WO 10/058322 | 5/2010 |
| WO | WO 14/086375 | 6/2014 |
| WO | WO 17/198699 | 11/2017 |
| WO | WO 18/104153 | 6/2018 |
| WO | WO 18/104154 | 6/2018 |
| WO | WO 18/206474 | 11/2018 |
| WO | WO 20/207908 | 10/2020 |
| WO | WO 21/257737 | 12/2021 |

OTHER PUBLICATIONS

Zhang [A Multifunctional Airflow Sensor Enabled by Optical Micro/nanofiber, Advanced Fiber Materials (2021) 3:359-367] (Year: 2021).*

Favero [Microstructured optical fiber interferometric breathing sensor, Journal of Biomedical Optics 17(3), 037006 (Mar. 2012)] (Year: 2012).*

Luo [Chip-scale optical airflow sensor, Microsystems & Nanoengineering ( 2022) 8:4] (Year: 2022).*

Author Unknown, "Biometric Technology Market Foresees Growth Due to Innovative Advancement," https://menafn.com/mf_contact.aspx?src=Contact_Authors, Dec. 18, 2020, 2 pages.

Guiliani et al., "Laser diode self-mixing technique for sensing applications," *Journal of Optics A: Pure and Applied Optics*, 2002, S283-S294.

* cited by examiner

NON-CONTACT RESPIRATION SENSING

CROSS-REFERENCE TO RELATED APPLICATIONS

This application is a nonprovisional and claims the benefit under 35 U.S.C. § 119(e) of U.S. Provisional Application No. 63/402,597, filed Aug. 31, 2022, and U.S. Provisional Patent Application No. 63/356,955, filed Jun. 29, 2022, the contents of which are incorporated herein by reference as if fully disclosed herein.

TECHNICAL FIELD

Embodiments described herein relate to non-contact respiration sensing, and in particular to non-contact respiration sensing using interferometric sensors.

BACKGROUND

Wearable devices such as smart watches, smart eyewear, virtual and/or augmented reality headsets, and the like, may include various sensors, which may sense physical phenomena such as movement, environmental conditions, and biometric data about a user. The data from sensors in a wearable device may be used to provide valuable information to a user, such as information about the activity and/or health of the user. Additional sensors in wearable devices may provide more robust information to a user and/or control or unlock additional applications of the wearable device. Given the wide range of applications for sensors in wearable devices, any new development in the configuration or operation of the sensors therein can be useful. New developments that may be particularly useful are developments that provide additional sensing capability while maintaining a small form factor.

SUMMARY

Embodiments described herein relate to non-contact respiratory sensing. In one aspect, a head mounted device may include a housing and one or more interferometric sensors disposed in the housing. The one or more interferometric sensors may be configured to emit electromagnetic radiation towards an expected airflow path for respiration of a user and generate one or more interferometric signals including information about particle movement in the expected airflow path for respiration of the user.

In one aspect, the head mounted device may further include processing circuitry communicably coupled to the one or more interferometric sensors and configured to determine respiration information about the user based on the one or more interferometric signals. In various aspects, the respiration information may include one or more of respiration rate, respiration velocity, respiration volume, respiration quality, whether a user is breathing through a nose or a mouth, information about particles inhaled, and information about particles exhaled.

In various embodiments, the one or more interferometric sensors may be self-mixing interferometric (SMI) sensors or Mach-Zender interferometric (MZI) sensors.

In one aspect, the head mounted device may further include one or more reference interferometric sensors. The one or more reference interferometric sensors may be configured to emit electromagnetic radiation towards an area outside the expected airflow path for respiration of the user and generate one or more reference interferometric signals including information about particle movement in the area outside the expected airflow path for respiration of the user. The processing circuitry may be communicably coupled to the one or more reference interferometric sensors and configured to determine the respiration information about the user based on the one or more interferometric signals and the one or more reference interferometric signals.

In one aspect, the one or more interferometric sensors comprise a first interferometric sensor and a second interferometric sensor. The first interferometric sensor may include one or more of a focal length, a depth of field, a numerical aperture, an angle of incidence with respect to a plane located in the expected airflow path for respiration of the user, and one or more characteristics of the electromagnetic radiation emitted therefrom that is different from the second interferometric sensor.

In one aspect, the head mounted device comprises a display. The processing circuitry may be coupled to the display and configured to cause the display to change in response to respiration of the user.

In one aspect, a method for operating a head mounted device may include generating, from a set of one or more interferometric sensors disposed in a housing of the head mounted device, one or more interferometric signals including information about particle movement caused by respiration of a user and determining, by processing circuitry in the head mounted device, respiration information about the user based on the one or more interferometric signals.

In one aspect, the respiration information may include one or more of respiration rate, respiration velocity, respiration volume, respiration quality, whether a user is breathing through a nose or mouth, information about particles inhaled, and information about particles exhaled.

In various aspects, the one or more interferometric sensors may be SMI sensors or MZI sensors.

In one aspect, the method further includes generating, from a set of one or more reference interferometric sensors disposed in the housing of the head mounted device, one or more reference interferometric signals including information about particle movement that is not caused by respiration of the user.

In one aspect, the respiration information about the user may be determined based on the one or more interferometric signals and the one or more reference interferometric signals.

In one aspect, a head mounted device may include a housing, one or more interferometric sensors, and a plurality of electromagnetic radiation detectors. The one or more interferometric sensors may be disposed in the housing and configured to emit electromagnetic radiation towards an expected airflow path for respiration of a user and generate one or more interferometric signals including information about particle movement in the expected airflow path for respiration of the user. The plurality of electromagnetic radiation detectors may be distributed in the housing and configured to generate one or more detector signals including information about reflections of the electromagnetic radiation emitted from the one or more interferometric sensors from one or more particles in the expected airflow path for respiration of the user.

In one aspect, the head mounted device may further include processing circuitry communicably coupled to the one or more interferometric sensors and the one or more electromagnetic radiation detectors. The processing circuitry may be configured to determine a particle size of one or more particles in the expected airflow path for respiration of the user based on the one or more interferometric signals and the one or more detector signals.

In one aspect, the processing circuitry may be further configured to determine respiration information about the user based on the one or more interferometric signals and the one or more detector signals.

In one aspect, the respiration information includes one or more of respiration rate, respiration velocity, respiration volume, respiration quality, whether a user is breathing through a nose or a mouth, information about particles inhaled, and information about particles exhaled.

BRIEF DESCRIPTION OF THE DRAWINGS

Reference will now be made to representative embodiments illustrated in the accompanying figures. It should be understood that the following descriptions are not intended to limit this disclosure to one included embodiment. To the contrary, the disclosure provided herein is intended to cover alternatives, modifications, and equivalents as may be included within the spirit and scope of the described embodiments, and as defined by the appended claims.

The use of the same or similar reference numerals in different figures indicates similar, related, or identical items.

Figure 1:
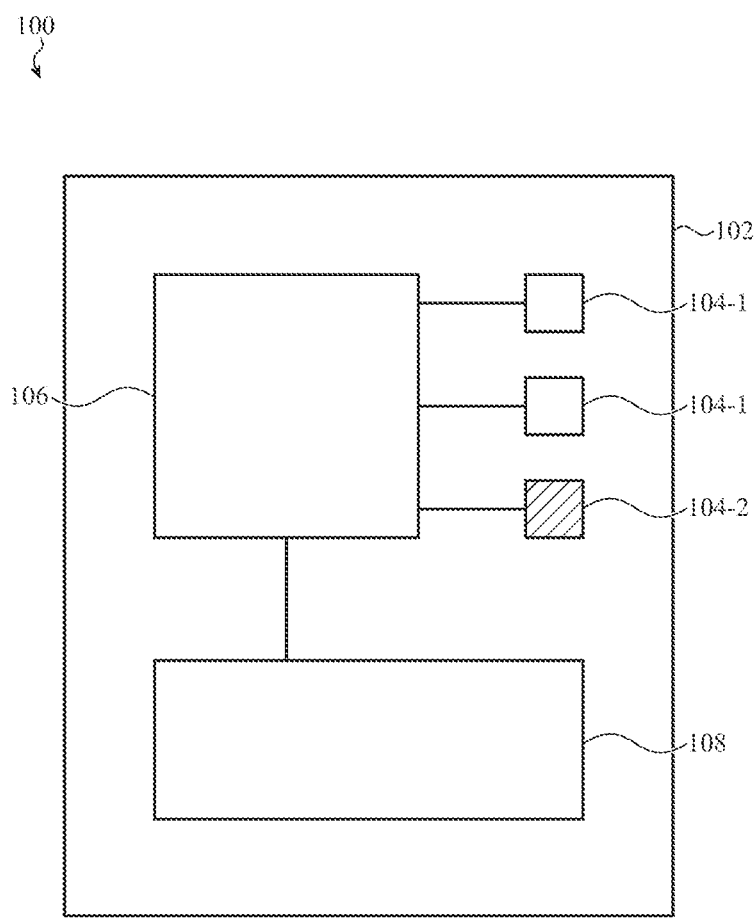
FIG. 1 shows an example electrical block diagram of a wearable device, such as described herein.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Coherent optical sensing, including Doppler velocimetry and heterodyning, can be used to measure physical phenomena including presence, distance, velocity, size, surface properties, and particle count. Interferometric sensors such as SMI sensors and MZI sensors may be used to perform coherent optical sensing. An SMI sensor is defined herein as a sensor that is configured to generate and emit light from a resonant cavity of a semiconductor light source, receive a reflection or backscatter of the light (e.g., light reflected or backscattered from an object) back into the resonant cavity, coherently or partially coherently self-mix the generated and reflected/backscattered light within the resonant cavity, and produce an output indicative of the self-mixing (i.e., an SMI signal). The generated, emitted, and received light may be coherent or partially coherent, but a semiconductor light source capable of producing such coherent or partially coherent light may be referred to herein as a coherent light source. The generated, emitted, and received light may include, for example, visible or invisible light (e.g., green light, infrared (IR) light, or ultraviolet (UV) light). The output of an SMI sensor (i.e., the SMI signal) may include a photocurrent produced by a photodetector (e.g., a photodiode). Alternatively or additionally, the output of an SMI sensor may include a measurement of a current or junction voltage of the SMI sensor's semiconductor light source.

Generally, an SMI sensor may include a light source and, optionally, a photodetector. The light source and photodetector may be integrated into a monolithic structure. Examples of semiconductor light sources that can be integrated with a photodetector include vertical cavity surface-emitting lasers (VCSELs), edge-emitting lasers (EELs), horizontal cavity surface-emitting lasers (HCSELs), vertical external-cavity surface-emitting lasers (VECSELs), quantum-dot lasers (QDLs), quantum cascade lasers (QCLs), and light-emitting diodes (LEDs) (e.g., organic LEDs (OLEDs), resonant-cavity LEDs (RC-LEDs), micro LEDs (mLEDs), superluminescent LEDs (SLEDS), and edge-emitting (ELEDs). These light sources may also be referred to as coherent light sources. A semiconductor light source may be integrated with a photodetector in an intra-cavity, stacked, or adjacent photodetector configuration to provide an SMI sensor.

Generally, SMI sensors have a small footprint and are capable of measuring myriad physical phenomena. Accordingly, they are useful in wearable devices, which are generally limited in size. As discussed above, a portion of the functionality of many wearable devices is directed to the measurement of biometric data about a user, such as heart rate and respiration rate. The small footprint of SMI sensors may enable additional sensing opportunities by allowing sensors to be placed in previously impractical locations, while the high accuracy of SMI sensors may enable the determination of rich biometric data.

MZI sensors are similar to SMI sensors, except that they include an electromagnetic radiation detector that is separate from an electromagnetic radiation source, and include an optical element configured to split electromagnetic radiation from the electromagnetic radiation source into a sensing portion and a feedback portion. The sensing portion of electromagnetic radiation is directed towards a desired target, where it is reflected and/or backscattered therefrom. The optical element is configured so that the reflected and/or backscattered part of sensing portion is mixed with the feedback portion. In some applications, an MZI sensor includes a balanced electromagnetic radiation detector that receives the reflected and/or backscattered part of the sensing portion and the feedback portion at different electromagnetic radiation detectors. The MZI sensor provides an interferometric output signal based on the mixed feedback portion and the reflected and/or backscattered part of the sensing portion.

As described in various embodiments herein, SMI sensors, or any other type of interferometric sensor, may be used to determine biometric data such as movement, and in particular muscle, ligament, tendon, and/or skin movement, and respiratory information such as respiration rate, respiration quality, information about nasal congestion, information about snoring, airflow velocity, and breathing volume. Placing and orienting SMI sensors in a head-mounted device so that they emit electromagnetic radiation towards an anatomical structure adjacent to a nasal passageway of a user may allow for the accurate determination of respiration information based on movement of the anatomical structure. For example, placing and orienting SMI sensors over a portion of the nose of the user may allow a head-mounted device such as smart eyewear, a virtual and/or augmented reality headset, a smart face-mask, and/or a smart nose clip to determine respiration information about a user.

SMI sensors may additionally or alternatively be used to detect intentional or unintentional movement of the face and/or nose of the user. Detection of unintentional facial movements may provide data useful for the diagnosis or monitoring of a health condition. Detection of intentional movements may be used to control various aspects of a device, such as navigating a user interface thereof.

Nasal and/or eye tissue, for example, of users can have various sensitivities, such as allergies, abrasion sensitivities, sensor and/or energy exposure sensitivities, etc. Accordingly, in some aspects described herein SMI sensors may be operated to emit electromagnetic radiation for sensing only when it is determined to be appropriate. For example, SMI sensors may be operated to emit electromagnetic radiation when they are in contact with a user's skin or the electromagnetic radiation emitted therefrom is otherwise unlikely to be directed at or towards a user's eyes. Accordingly, wearable devices described herein may detect when it is appropriate to emit electromagnetic radiation from a particular SMI sensor or sensors and enable and disable the emission of electromagnetic radiation therefrom accordingly.

Additionally, SMI sensors, MZI sensors, or any other type of interferometric sensor, may be used to determine respiration information such as respiration rate, respiration velocity, respiration volume, respiration quality, whether a user is breathing through their nose or mouth, information about particles inhaled (e.g., particle size, particle count), and information about particles exhaled (e.g., particle size, particle count). In particular, sensors may be positioned and oriented in a head-mounted device to emit electromagnetic radiation towards an expected airflow path for respiration of a user, and generate one or more interferometric signals including information about particle movement in the area. As discussed herein, particles may be liquid matter or solid matter. Further as discussed herein, airflow is a gaseous flow that may carry particles. The one or more interferometric signals may be used to determine the aforementioned respiration information, as well as additional information. In some aspects, multiple interferometric sensors may be positioned and oriented in a head mounted device in order to differentiate between nose and mouth breathing of a user, as well as to differentiate between airflow due to respiration of a user and ambient airflow in the environment in which the user is located.

The foregoing and other embodiments are discussed below with reference to FIGS. 1-15. However, those skilled in the art will readily appreciate that the detailed description given herein with respect to these figures is for explanation only and should not be construed as limiting.

Directional terminology, such as "top", "bottom", "upper", "lower", "front", "back", "over", "under", "above", "below", "left", or "right" is used with reference to the orientation of some of the components in some of the figures described below. Because components in various embodiments can be positioned in a number of different orientations, directional terminology is used for purposes of illustration only and is usually not limiting. The directional terminology is intended to be construed broadly, and therefore should not be interpreted to preclude components being oriented in different ways. Also, as used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

FIG. 1 shows an exemplary wearable device 100. The wearable device 100 includes a housing 102, a number of sensors 104 disposed in the housing 102, processing circuitry 106 communicably coupled to the sensors 104, and a display 108, which is also communicably coupled to the processing circuitry 106. The sensors 104 may include a number of SMI sensors 104-1 and a proximity sensor 104-2. While two SMI sensors 104-1 and one proximity sensor 104-2 are shown for purposes of illustration, the wearable device 100 may include any number of SMI sensors 104-1 and any number of proximity sensors 104-2. Further, the wearable device 100 may include any number of additional sensors, which are not shown. As discussed herein, the sensors 104 may be positioned and oriented in the housing 102 to emit electromagnetic radiation towards an anatomical structure adjacent a nasal passageway of the user. For example, the sensors 104 may be positioned and oriented to be over or otherwise near the nose of the user when the wearable device 100 is being worn. The display 108 may be positioned to be in front an eye of the user. In some aspects of the present disclosure, two displays 108 may be provided, one in front of each eye of the user. In another aspect, the wearable device 100 does not include a display, and the user may interact with the wearable device 100 using a non-visual user interface (e.g., voice control) or interact with the wearable device 100 via a device that is communicably coupled to the wearable device 100 (e.g., via a wired or wireless connection).

The SMI sensors 104-1 may be operated to emit electromagnetic radiation toward an anatomical structure of the user adjacent a nasal passageway. For example, the SMI sensors 104-1 may be positioned and oriented to emit electromagnetic radiation toward tissue adjacent, surrounding, or otherwise near the nasal passageway of the user. The tissue may be bone or soft tissue. For example, the SMI sensors 104-1 may be positioned and oriented to emit electromagnetic radiation towards a nasal bone of the user, an upper lateral cartilage of the nose of the user, a lower lateral cartilage of the nose the user, and/or the skin on and/or around the nose of the user. The SMI sensors 104-1 may be positioned and oriented to be directly against the skin of the user, or there may be an air gap present between the SMI sensors 104-1 and the skin of the user. The electromagnetic radiation emitted from the SMI sensors 104-1 may be configured to reflect and/or backscatter from the tissue of the user or penetrate the tissue of the user to a desired depth, passing through some tissue (e.g., skin) with minimal or low reflection and/or backscatter, while reflecting and/or backscattering off other tissue (e.g., cartilage or bone) to a greater degree. For example, some characteristics of the electromagnetic radiation (e.g., wavelength) and/or a focal length of the SMI sensors 104-1 may be configured to measure movement of a desired anatomical structure. In some aspects, different ones of the SMI sensors 104-1 may be configured to emit electromagnetic radiation that reflects and/or backscatters primarily from different anatomical structures, either by the position and orientation of the SMI sensors 104-1 in the housing 102, or by the characteristics of the electromagnetic radiation emitted therefrom.

The electromagnetic radiation emitted from the SMI sensors 104-1 may be modulated or non-modulated. The modulation, or lack of modulation, of the electromagnetic radiation may allow for the detection of different physical phenomena. For example, a first modulation pattern of the electromagnetic radiation emitted from the SMI sensors 104-1 may be useful for detecting the proximity of an object to the SMI sensors 104-1, while a second modulation pattern of the electromagnetic radiation emitted from the SMI sensors 104-1 may be useful for detecting movement (e.g., velocity) of an object. In various aspects, the SMI sensors 104-1 may be operated such that the electromagnetic radiation emitted therefrom is modulated in the same or different ways in order to detect desired physical phenomena.

The electromagnetic radiation emitted from an SMI sensor 104-1 may be partially reflected and/or backscattered from a desired anatomical structure back towards the SMI sensor 104-1. The reflected and/or backscattered electromagnetic radiation may self-mix (or interfere) with the generated electromagnetic radiation. The self-mixing may be measured (e.g., by measuring the electromagnetic radiation with a photodetector or by measuring a current and/or junction voltage of a light source of the SMI sensor 104-1) to generate an SMI signal. By generating the electromagnetic radiation via specific drive patterns (e.g., via doppler and/or triangular drive patterns) and measuring the reflection and/or backscatter thereof, SMI signals may include information about movement of the desired anatomical structure.

The proximity sensor 104-2 may detect the proximity of the wearable device 100 to the user, which is indicated in a proximity signal provided to the processing circuitry 106. The proximity sensor 104-2 may be any suitable type of proximity sensor, such as, for example, an ultrasonic sensor, an infrared sensor, a capacitive sensor, or a resistive sensor. In general, it may be desirable for the proximity sensor 104-2 to be a type of proximity sensor that prevents the SMI sensor 104-1 from emitting electromagnetic radiation, as discussed herein.

As discussed above, the desired anatomical structure may be adjacent a nasal passageway of the user. For example, the desired anatomical structure may be the nasal bone, the upper lateral cartilage of the nose, the lower lateral cartilage of the nose, and/or the skin on and/or around the nose. The processing circuitry 106 may use the information about movement of the desired anatomical structure in the SMI signals to determine respiration information about the user. For example, the processing circuitry 106 may use the information about movement of the desired anatomical structure to determine respiration rate, respiration quality, information about nasal congestion (e.g., a degree of nasal congestion), information about snoring (e.g., the presence or absence of snoring, a severity of snoring), airflow velocity, and breathing volume. The processing circuitry 106 may determine respiration information from the SMI signals in any suitable manner, such as, for example, by providing the SMI signals to a machine learning model.

In addition to respiration information, the processing circuitry 106 may also use the SMI signals to determine voluntary or involuntary facial movements of the user. For example, the processing circuitry 106 may use the SMI signals to detect facial tics of a user, which may provide information for the diagnosis or monitoring of some health conditions. Additionally, the processing circuitry 106 may use the SMI signals to detect intentional facial movements, such as a movement of the nose. Detected intentional facial movements may be used, for example, as a user input to the wearable device 100. For example, intentional facial movements of the user, in addition to other types of user input, may be used to change or otherwise navigate a user interface shown on the display 108 of the wearable device 100. Notably, the display 108 may be omitted in some aspects and intentional facial movements may be used as a user input to control or otherwise operate the wearable device 100 in any suitable manner.

While not shown, the wearable device 100 may include any number of user input elements such as buttons, microphones, speakers, or the like. The wearable device 100 may also include additional structural elements such as straps, bands, or other suitable elements for positioning, attaching, or securing the wearable device 100 to the user. The wearable device 100 may also include additional circuitry, such as additional sensors, communication circuitry (e.g., wired or wireless communication circuitry), or any other circuitry to facilitate the operation and functionality of the wearable device 100.

The wearable device 100 may be a head-mounted device. Accordingly, the housing 102 of the wearable device 100 may be shaped and sized to be mounted to the head of a user. One or more straps or other mounting structures (not shown) may be used to affix the wearable device 100 to the head of the user. In various aspects discussed herein, the housing 102 may be sized and shaped to provide eyewear, a virtual and/or augmented reality headset, a face mask, and a nose clip. However, the form factor of the wearable device 100 may be provided in any suitable shape and size without departing from the principles herein.

Figure 2A:
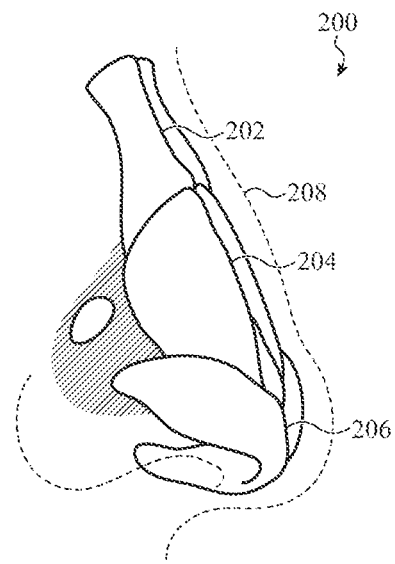
FIGS. 2A and 2B show an anatomical views of a nose, such as described herein.
Figure 2B:
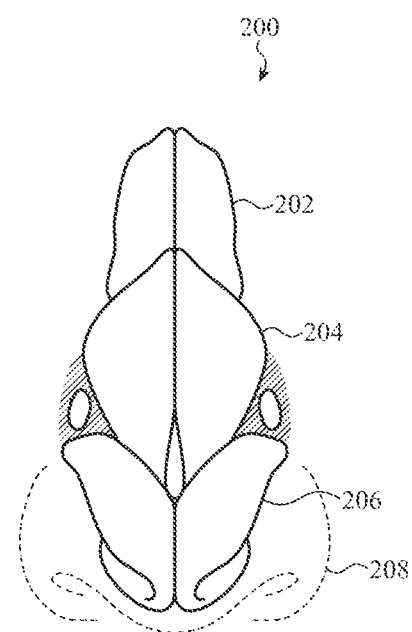

FIGS. 2A and 2B show anatomical views of a nose 200 of a user. In particular, FIG. 2A shows an anatomical view of a nose of a user along a sagittal plane, while FIG. 2B shows an anatomical view of a nose of a user along a frontal plane. The nose 200 includes a nasal bone 202, an upper lateral cartilage 204, and a lower lateral cartilage 206. The nasal bone 202, upper lateral cartilage 204, and lower lateral cartilage 206 are covered with skin 208. In various aspects of the present disclosure, SMI sensors such as those discussed herein may be positioned and oriented in a wearable device such that they emit electromagnetic radiation towards one or more of the nasal bone 202, the upper lateral cartilage 204, the lower lateral cartilage 206, and the skin 208 on or around the nose 200. Movement of any one of the nasal bone 202, the upper lateral cartilage 204, the lower lateral cartilage 206, and the skin 208 on or around the nose 200 may be indicative of various respiration information about the user such as respiration rate, respiration quality, information about nasal congestion (e.g., a degree of nasal congestion), information about snoring (e.g., the presence or absence of snoring, severity of snoring), airflow velocity, and breathing volume. As discussed herein, the electromagnetic radiation emitted from the SMI sensors may be configured (e.g., via wavelength, focal length, etc.) to primarily reflect and/or backscatter from a particular one of the aforementioned anatomical structures, or any other anatomical structure, and measured to generate SMI signals that are used to determine the respiration information. Further, the SMI signals may be used to detect voluntary and involuntary nose and/or facial movements.

Figure 3:
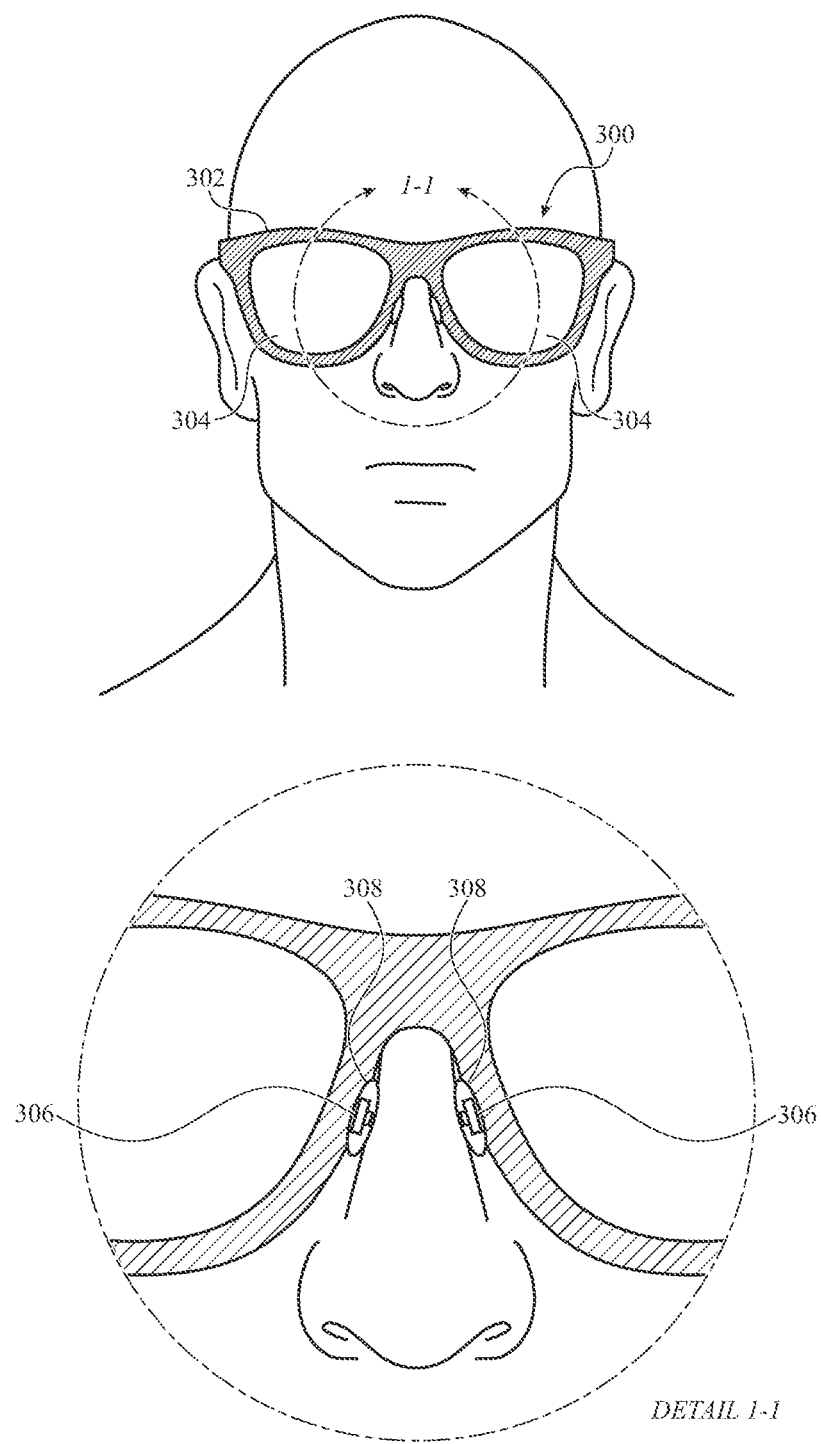
FIG. 3 shows an exemplary wearable device being worn by a user, such as described herein.

FIG. 3 shows a wearable device 300 being worn by a user according to an additional aspect of the present disclosure. The wearable device 300 shown in FIG. 3 is in the form factor of eyewear, and thus may include a frame 302, a pair of lenses 304, and a number of sensors 306, which may be positioned and oriented in nosepieces 308 coupled to the frame 302 such that they are over or near the nose of the user. An enlarged view of the nosepieces 308 including the sensors 306 is shown in FIG. 3. The sensors 306 may be positioned and oriented so that they emit electromagnetic radiation towards an anatomical structure adjacent a nasal passageway of the user. The sensors 306 may be positioned and oriented in the nosepieces 308 such that they are in direct contact with the skin of the user or such that there is an air gap between the sensors 306 and the skin of the user. The sensors 306 may be SMI sensors or include at least one SMI sensor along with one or more other types of sensors, such as a proximity sensor. The sensors 306 may be operated as discussed herein to detect movement of an anatomical structure of a user, determine respiration information about the user, detect intentional and/or unintentional facial movements of the user, and operate appropriately to avoid irritating a user. While the nosepieces 308 are shown as separate pieces coupled to the frame 302, in some aspects the nosepieces 308 may be molded into or otherwise integrated with the frame 302. While not shown, the wearable device 300 may include a display, which may be projected or otherwise provided on one or both of the lenses 304. In some aspects, the wearable device 300 may not include a display. Further, the wearable device 300 may include processing circuitry to operate the sensors 306 as discussed herein, additional circuitry, additional user input elements such as buttons, microphones, speakers, and cameras, and/or additional structural elements. In general, FIG. 3 is meant to illustrate an exemplary form factor of a wearable device 300 as discussed herein, as well as the placement of sensors 306 in the exemplary form factor.

Figure 4:
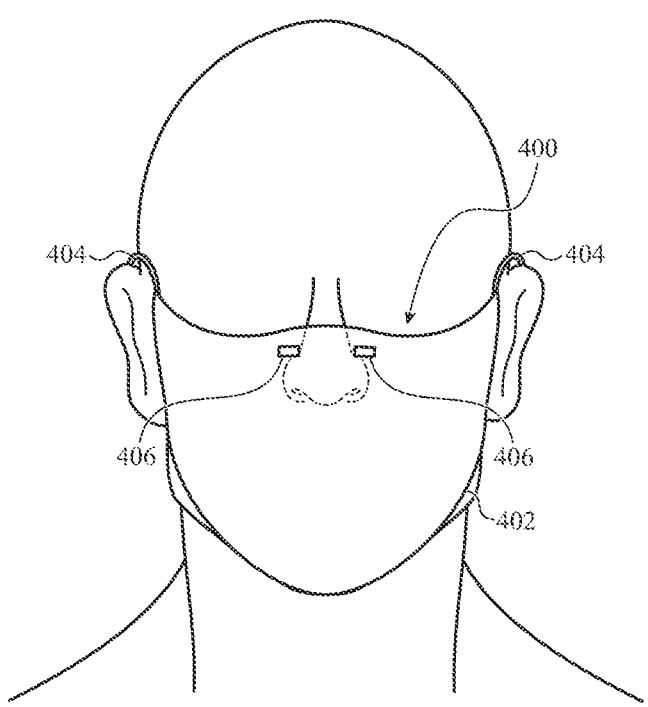
FIG. 4 shows an exemplary wearable device being worn by a user, such as described herein.

FIG. 4 shows a wearable device 400 being worn by a user according to an additional aspect of the present disclosure. The wearable device 400 shown in FIG. 4 is in the form factor of a face mask, and thus may include a cover 402, a number of straps 404 coupled to the cover 402 and configured to attach the cover 402 over the nose and/or mouth of the user, and a number of sensors 406 disposed in the cover 402. The sensors 406 may be positioned and oriented to be over or near the nose of the user. In particular, the sensors 406 may be positioned and oriented to emit electromagnetic radiation towards an anatomical structure adjacent a nasal passageway of the user. In various aspects, the sensors 406 may be in direct contact with the skin of the user or there may be an air gap between the sensors 406 and the skin of the user. The sensors 406 may be SMI sensors or include at least one SMI sensor along with one or more other types of sensors, such as a proximity sensor. The sensors 406 may be operated as discussed herein to detect movement of an anatomical structure of a user, determine respiration information about the user, detect intentional and/or unintentional facial movements of the user, and operate appropriately to avoid irritating a user. While not shown, the wearable device 400 may include additional components such as a display, processing circuitry to operate the sensors 406 as discussed herein, additional circuitry, additional user input elements such as buttons, microphones, speakers, and cameras, and/or additional structural elements. In general, FIG. 4 is meant to illustrate an exemplary form factor of a wearable device 400 as discussed herein, as well as the placement of sensors 406 in the exemplary form factor.

Figure 5A:
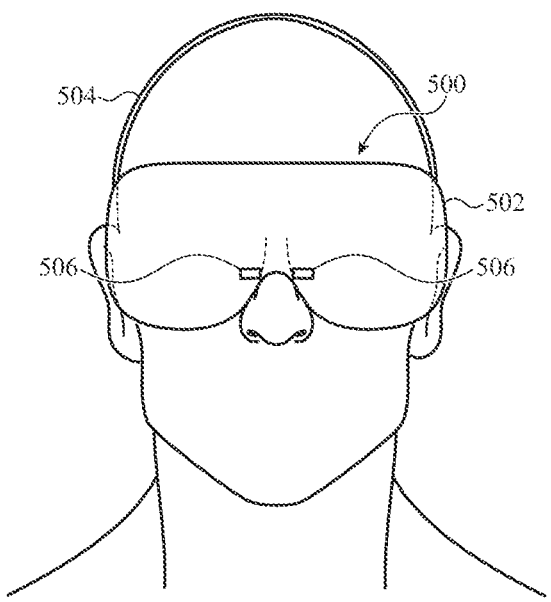
FIGS. 5A and 5B show an exemplary wearable device being worn by a user, such as described herein.
Figure 5B:
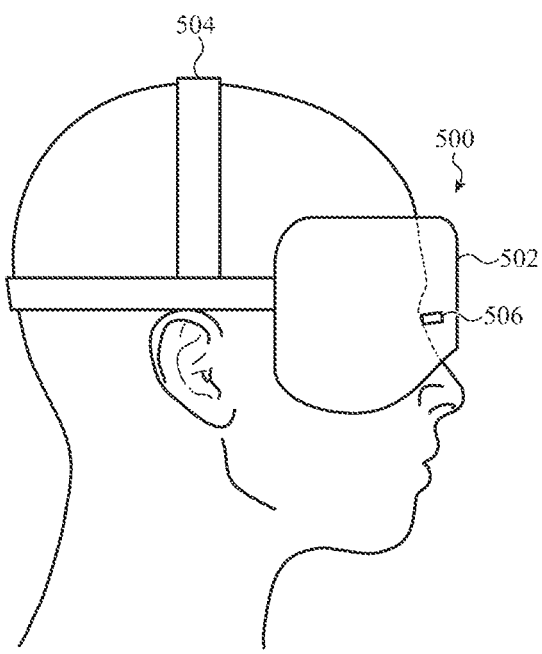

FIGS. 5A and 5B show a wearable device 500 being worn by a user according to an additional embodiment of the present disclosure. In particular, FIG. 5A shows a front view and FIG. 5B shows a side view of the wearable device 500 being worn by the user. The wearable device 500 shown in FIGS. 5A and 5B is in the form factor of a virtual and/or augmented reality headset, and thus may include a housing 502, a strap 504 for attaching the housing 502 to the head of the user, and a number of sensors 506 disposed in the housing 502. The sensors 506 may be positioned and oriented to be over or near the nose of the user. In particular, the sensors 506 may be positioned and oriented to emit electromagnetic radiation towards an anatomical structure adjacent a nasal passageway of the user. In various aspects, the sensors 506 may be in direct contact with the skin of the user or there may be an air gap between the sensors 506 and the skin of the user. The sensors 506 may be SMI sensors or include at least one SMI sensor along with one or more other types of sensors, such as a proximity sensor. The sensors 506 may be operated as discussed herein to detect movement of an anatomical structure of a user, determine respiration information about the user, detect intentional and/or unintentional facial movements of the user, and/or operate appropriately to avoid irritating a user. While not shown, the wearable device 500 may include additional components such as displays, processing circuitry to operate the displays and sensors 506 as discussed herein, additional circuitry, additional user input elements such as buttons, microphones, speakers, and cameras, and/or additional structural elements. In general, FIGS. 5A and 5B are meant to illustrate an exemplary form factor of a wearable device 500 as discussed herein, as well as the placement of sensors 506 in the exemplary form factor.

While FIGS. 3-5B illustrate various exemplary form factors of a wearable device, they are not meant to be exhaustive. The present disclosure contemplates any form factor for a wearable device capable of positioning SMI sensors as discussed herein, including swimming goggles, safety eyewear, or any other suitable form factor.

Figure 6:
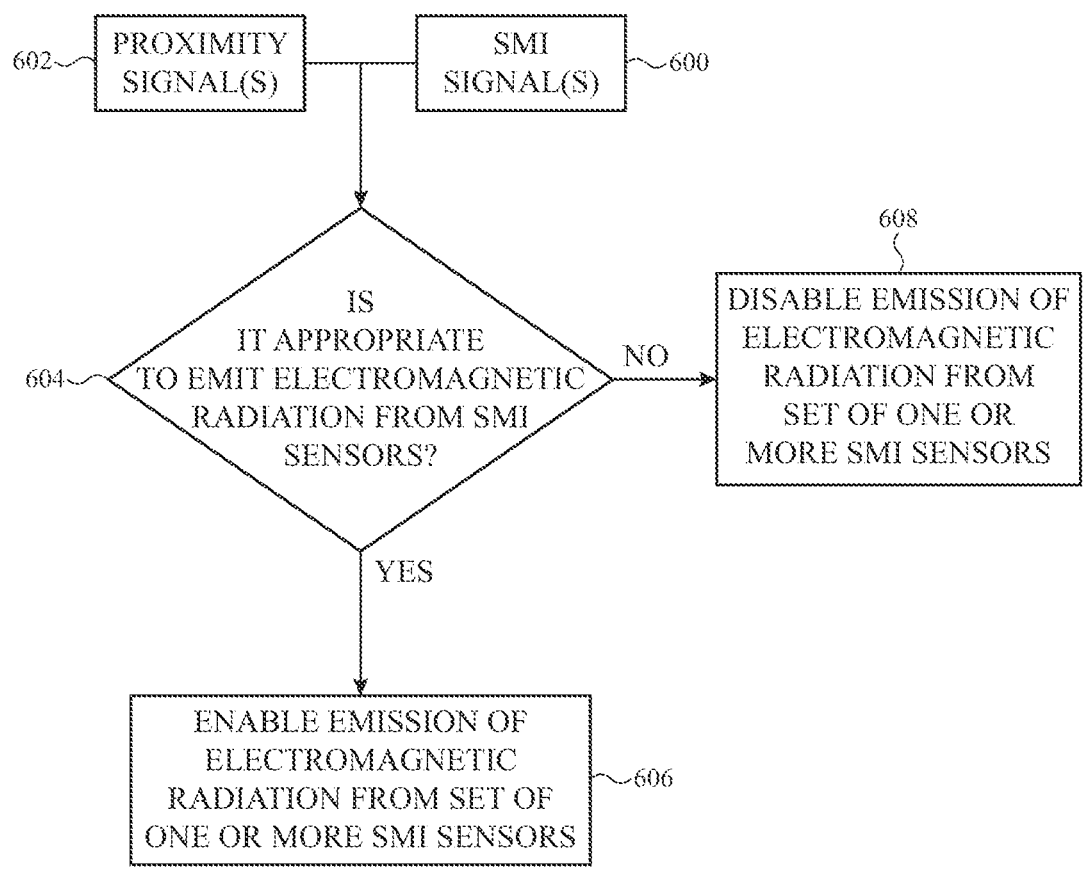
FIG. 6 is a flow diagram illustrating a method of operating a wearable device, such as described herein.

As discussed herein, SMI sensors may be placed over or near the nose of a user to determine valuable information such as respiration information as well as voluntary or involuntary nose and/or facial movements. In some instances, some users may be especially sensitive to electromagnetic radiation, and thus placing SMI sensors in close proximity to the eyes of the user may require additional considerations. Accordingly, FIG. 6 is a flow diagram illustrating a method of operating a wearable device according to one aspect of the present disclosure. One or more SMI signals are received from one or more SMI sensors (step 600). Additionally or alternatively, one or more proximity signals are received from one or more proximity sensors (step 602). The one or more SMI signals and/or the one more proximity signals are used by processing circuitry of the wearable device to determine if it is appropriate to emit electromagnetic radiation from the one or more SMI sensors (step 604). Determining if it is appropriate to emit electromagnetic radiation from the one or more SMI sensors may include determining if the wearable device is being worn by the user, or is being properly worn by the user (e.g., the SMI sensors and/or proximity sensors are directly against the skin of the user). Such a determination may be accomplished in any suitable manner, including comparing the SMI signals and/or proximity signals to a threshold value, making calculations based on the SMI signals and/or proximity signals, providing the SMI signals and/or proximity signals to a machine learning model, etc. If it is appropriate to emit electromagnetic radiation from the one or more SMI sensors, the processing circuitry may enable the emission of electromagnetic radiation from the one or more SMI sensors (step 606). Alternatively, if it is not appropriate to emit electromagnetic radiation from the one or more SMI sensors or there is not sufficient information from the proximity sensor, the processing circuitry may disable the emission of electromagnetic radiation from the one or more SMI sensors (step 608).

The foregoing process may be repeated at a predetermined interval, or initiated in response to a detected event such as significant movement of the wearable device, which may be detected by one or more additional sensors such as an accelerometer. Operating the SMI sensors of a wearable device in this manner may improve the safety profile, battery life, and/or efficacy of the device. The principles of operation described with respect to FIG. 6 may be used in any of the wearable devices described herein.

Figure 7:
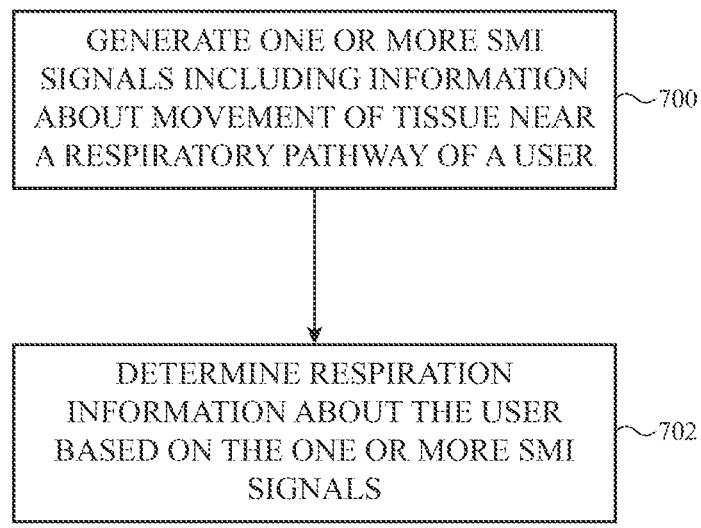
FIG. 7 is a flow diagram illustrating a method of operating a wearable device, such as described herein.

The wearable devices discussed herein may determine respiration information about a user based on SMI sensors positioned on or near the nose of the user. However, the present disclosure contemplates the broader use of information about movement of tissue near a respiratory pathway of a user to determine respiration information about the user. To illustrate these principles, FIG. 7 is a flow diagram describing a method for operating a wearable device to obtain respiration information about a user according to one aspect of the present disclosure. First, one or more SMI signals are generated, where the one or more SMI signals include information about the movement of tissue near a respiratory pathway of a user (step 700). The movement of the tissue may be a vibration of the tissue. The tissue may be soft tissue such as skin, cartilage, muscle, tendon, or ligament, or hard tissue such as bone. The one or more SMI signals may be generated from one or more SMI sensors in the wearable device. The one or more SMI sensors may be positioned and oriented to be over or near the respiratory pathway of the user. The respiratory pathway may be a nasal passageway of the user.

Next, respiration information about the user is determined based on the one or more SMI signals (step 702). The respiration information may be determined, for example, by providing the one or more SMI signals to a machine learning model. In general, any suitable calculation, transformation, or the like may be performed to determine the respiration information from the one or more SMI signals. The respiration information may include one or more of respiration rate, respiration quality, information about nasal congestion (i.e., degree of nasal congestion), information about snoring (e.g., presence or absence of snoring, severity of snoring), airflow velocity, and breathing volume. The respiration information may be useful to the user for the diagnosis or monitoring of some health conditions. In some aspects, the respiration information may be displayed graphically for the user. The wearable device may use the respiration information to notify the user of certain events, such as when the user is experiencing a particular level of nasal congestion (which may be indicative of seasonal allergies and/or illness), when the user is breathing through the mouth rather than the nose, etc. Further, visualizations of the user's breathing may be generated and shown to the user, which may aid in activities such as guided breathing instruction or biofeedback. If it is detected that a user stops breathing, emergency services can be contacted to provide medical aid, in some cases automatically. The principles of operation described with respect to FIG. 7 may be used in any of the wearable devices described herein.

In addition to determining respiration information, data from SMI sensors positioned and oriented to be over or near a respiratory pathway may be used along with complimentary data streams from other sensors to obtain or discern additional information about a user. The other sensors may be located in the wearable device itself, in a different wearable device worn by the user, in a wearable device worn by another user, or in a non-wearable device. For example, data from a wrist-worn wearable device worn by the user may be combined with data from SMI sensors in a wearable device as described herein to obtain additional information about the user. Further, data from a non-wearable device, such as a device in the environment around a user may be combined with data from SMI sensors in a wearable device as described herein to obtain additional information about the user. Data from a wearable device worn by a different user may also be combined with data from SMI sensors in a wearable device as described herein to enable additional functionality (e.g., improved gaming experiences between users). In one example, blood oxygen saturation information from a blood oxygen saturation sensor in a wearable device worn by the user may be combined with respiration information obtained as discussed herein. The blood oxygen saturation information may enrich the respiration information to enable discernment of respiration events such as a user holding their breath versus a user choking or drowning. Gaze tracking information may be combined with respiration information to determine information about a user such as attentiveness and focus on a task (e.g., student or driver focus), which may enable a user to be notified to take a break as attentiveness wanes. Respiration information, alone or combined with other information about a user, may enable a wearable device to provide breathing queues (e.g., when to breathe in, when to hold breath, when to breathe out, and breathing pacing), either for general health or related to a particular task such as for improving performance in sporting or other activities (e.g., swimming, diving, golf, tennis, archery, and baseball).

Respiration information, along with other complimentary information, may also be used to track a user's breathing or health trends over time. Such information may be indicative of training capacity and whether a particular training regimen is effective for a user. Respiration information, along with other complimentary information, may also provide an unobtrusive way to monitor an emotional response of a user, for example, by detecting gasping, laughter, crying, sobbing, speech and speech emphasis, etc. Monitoring emotional response via respiration information may be less obtrusive than directly monitoring audio. Emotional response information may in turn be useful in determining a user's response to various environmental stimuli or medications, which a user may wish to track over time.

Figure 8:
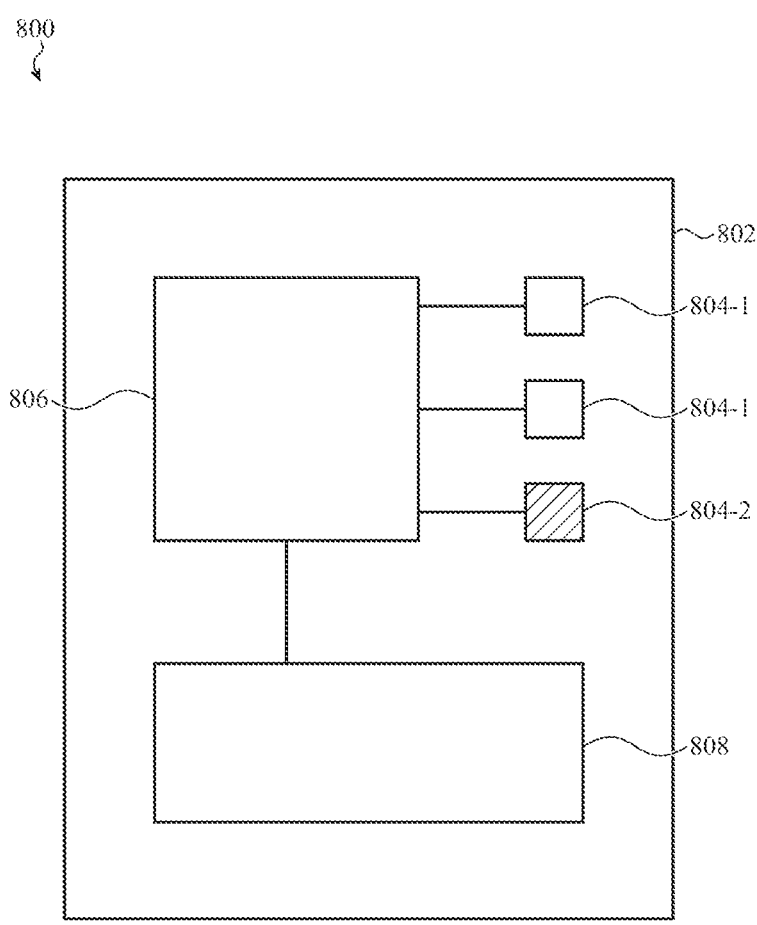
FIG. 8 shows an example electrical block diagram of a wearable device, such as described herein.

While FIGS. 1-7 primarily discuss the use of SMI sensors to determine respiration information and/or movement information in the context of a wearable device, any interferometric sensors, such as MZI sensors, can be used to achieve similar results. Further, interferometric sensors may be positioned and oriented in a housing of a wearable device to measure other physical phenomena. In one aspect, interferometric sensors may be positioned and oriented in a wearable device to detect respiration of a user without contact. In particular, interferometric sensors may be positioned and oriented in a housing of a head mounted device to sense particle movement caused by respiration of a user. FIG. 8 shows an exemplary wearable device 800 configured in this manner. The wearable device 800 includes a housing 802, a number of sensors 804 disposed in the housing 802, processing circuitry 806 communicably coupled to the sensors 804, and an optional display 808, which is also communicably coupled to the processing circuitry 806. The sensors 804 may include a number of interferometric sensors 804-1 and, optionally, one or more electromagnetic radiation detectors 804-2. While two interferometric sensors 804-1 and one electromagnetic radiation detector 804-2 are shown for purposes of illustration, the wearable device 800 may include any number of interferometric sensors 804-1 and any number of electromagnetic radiation detectors 804-2. Further, the wearable device 800 may include any number of additional sensors, which are not shown. As discussed herein, the interferometric sensors 804-1 may be positioned and oriented in the housing 802 to emit electromagnetic radiation towards an expected airflow path for respiration of a user. For example, the sensors 804-1 may be positioned and oriented to emit electromagnetic radiation towards an area in front of the mouth of a user, and/or below a nose of the user where air would normally flow during respiration. The display 808 may be positioned to be in front of an eye of the user. In some aspects, two displays 808 may be provided, one in front of each eye of the user. In another aspect, the wearable device 800 does not include a display, and the user may interact with the wearable device 800 using a non-visual user interface (e.g., voice control) or interact with the wearable device 800 via a device that is communicably coupled to the wearable device 800 (e.g., via a wired or wireless connection).

The electromagnetic radiation emitted from the interferometric sensors 804-1 may be modulated or non-modulated. The modulation, or lack of modulation, of the electromagnetic radiation may allow for the detection of different physical phenomena. For example, a first modulation pattern of electromagnetic radiation emitted from the interferometric sensors 804-1 may be useful for detecting the proximity of an object to the interferometric sensors 804-1, while a second modulation pattern of the electromagnetic radiation emitted from the interferometric sensors 804-1 may be useful for detecting movement (e.g., velocity) of an object. In various aspects, the interferometric sensors 804-1 may be operated such that the electromagnetic radiation emitted therefrom is modulated in the same or different ways in order to detect desired physical phenomena. In one aspect, the electromagnetic radiation emitted from the interferometric sensors 804-1 is modulated in a frequency modulated continuous wave (FMCW) mode, wherein the instantaneous frequency of the electromagnetic radiation is swept during signal integration.

The interferometric sensors 804-1 may each be configured with a particular focal length, depth of field, numerical aperture, angle of incidence (e.g., with respect to a reference plane), wavelength of electromagnetic radiation emitted, and modulation of electromagnetic radiation emitted. In some aspects, at least one of the focal length, depth of field, numerical aperture, angle of incidence, wavelength of electromagnetic radiation emitted, and modulation of electromagnetic radiation emitted, are different between the interferometric sensors 804-1.

The electromagnetic radiation emitted from an interferometric sensor 804-1 may be partially reflected and/or backscattered from particles in the expected airflow path for respiration of the user back towards the interferometric sensor 804-1. The reflected and/or backscattered electromagnetic radiation may be mixed with a reference signal (as discussed with respect to SMI and MZI sensors herein) to produce an interferometric signal that is indicative of particle movement in the area. By generating the electromagnetic radiation via specific drive patterns (e.g., via doppler and/or triangular drive patterns) and measuring the reflection and/or backscatter thereof, interferometric signals may include information about respiration of the user.

The one or more electromagnetic radiation detectors 804-2 may be positioned and oriented in the housing 802 to sense off-axis reflections and/or backscattering of electromagnetic radiation emitted by the interferometric sensors 804-1. This may enable scatterometry for particle size tracking of particles inhaled and/or exhaled by a user of the wearable device 800.

While not shown, the wearable device 800 may include any number of user input elements such as buttons, microphones, speakers, and the like. The wearable device 800 may also include additional structural elements such as straps, bands, or other suitable elements for positioning, attaching, or securing the wearable device 800 to the user. The wearable device 800 may also include additional circuitry, such as additional sensors, communication circuitry (e.g., wired or wireless communication circuitry), or any other circuitry to facilitate the operation and functionality of the wearable device 800.

The wearable device 800 may be head mounted device. Accordingly, the housing 802 of the wearable device 800 may be shaped and sized to be mounted to the head of a user. One or more straps or other mounting structures (not shown) may be used to affix the wearable device 800 to the head of the user. In various aspects discussed herein, the housing 802 may be sized and shaped to provide eyewear, a virtual and/or augmented reality headset, a face mask, and a nose clip. However, the form factor of the wearable device 800 may be provided in any suitable shape and size without departing from the principles herein.

Figure 9:
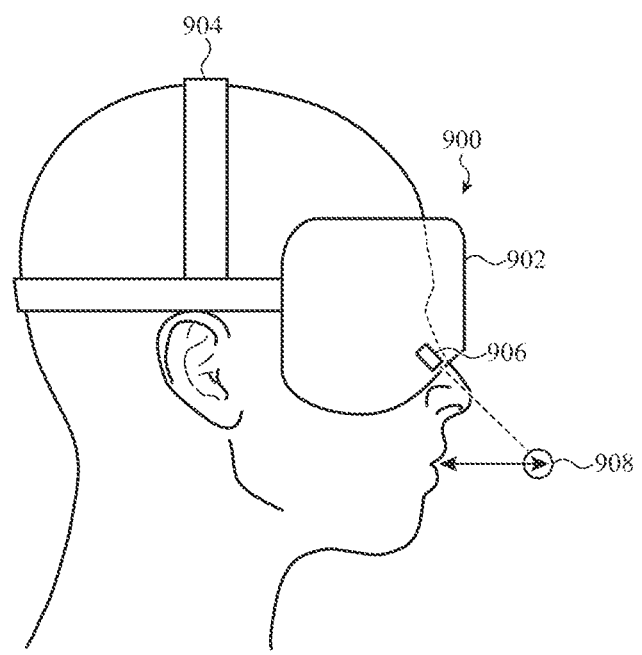
FIGS. 9-12 show an exemplary wearable device being worn by a user, such as described herein.

FIG. 9 shows a side view of a wearable device 900 being worn by a user according to one embodiment of the present disclosure. The wearable device 900 is in the form factor of a virtual and/or augmented reality headset, and thus may include a housing 902, a strap 904 for attaching the housing 902 to the head of the user, and an interferometric sensor 906 disposed in the housing 902. The interferometric sensor 906 may be positioned and oriented towards an area 908 in front of the mouth and/or nose of the user that is expected to experience airflow due to respiration of the user (i.e., an expected airflow path for respiration of the user) such that the interferometric sensor 906 emits electromagnetic radiation towards the area 908 in which airflow due to respiration is expected. The interferometric sensor 906 may be operated as discussed herein to detect movement of particles in the area 908 experiencing airflow in order to determine respiration information about the user. While not shown, the wearable device 900 may include additional components such as displays, processing circuitry to operate the displays and interferometric sensors 906 as discussed herein, additional circuitry, additional user input elements such as buttons, microphones, speakers, and cameras, and/or additional structural elements. In general, FIG. 9 is meant to illustrate an exemplary form factor of a wearable device 900 as discussed herein, as well as the placement of an interferometric sensor 906 in the exemplary form factor.

Figure 10:
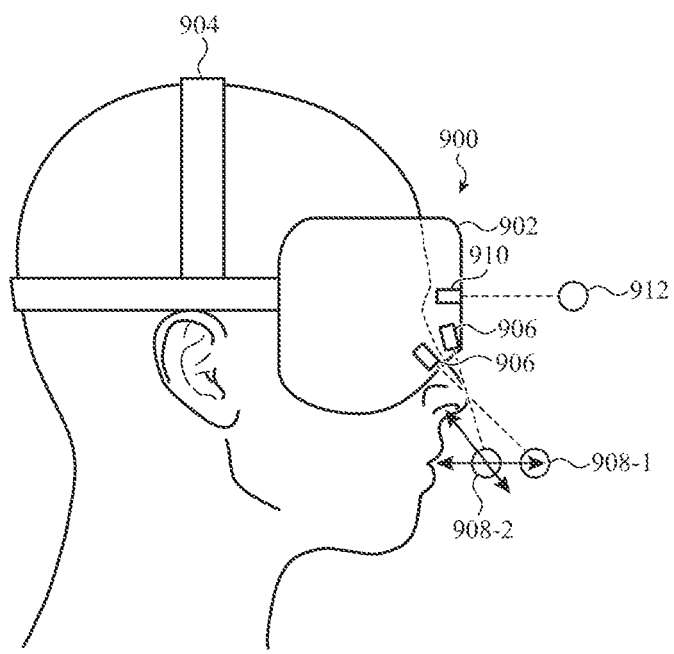

FIG. 10 shows a side view of the wearable device 900 being worn by the user according to an additional embodiment of the present disclosure. The wearable device 900 shown in FIG. 10 is similar to that shown in FIG. 9, but illustrates two interferometric sensors 906 and a reference sensor 910. The interferometric sensors 906 may be positioned and oriented in the housing 902 such that a first one of the interferometric sensors 906 emits electromagnetic radiation towards a first area 908-1 in front of the mouth of the user, while a second one of the interferometric sensors 906 emits electromagnetic radiation towards a second area 908-2 in front of the nose of the user. The first area 908-1 may experience airflow primarily due to mouth breathing of the user, while the second area 908-2 may experience airflow due to both nose and mouth breathing of the user. By positioning and orienting the interferometric sensors 906 in this or a similar manner, the wearable device 900 may be able to differentiate nose and mouth breathing of the user, which may be useful in some situations.

The reference sensor 910 may be positioned and oriented in the housing 902 towards an area 912 outside of an expected airflow path for respiration of the user. The reference sensor may also be an interferometric sensor configured to emit electromagnetic radiation towards the area 912 outside the expected airflow path for respiration of the user and thus may sense particle movement in this area 912. Particle movement in the area 912 outside the expected airflow path for respiration of the user may be indicative of airflow (e.g., due to wind or air conditioning) that is not involved in respiration, and thus may enable more accurate determination of respiration information.

Figure 11:
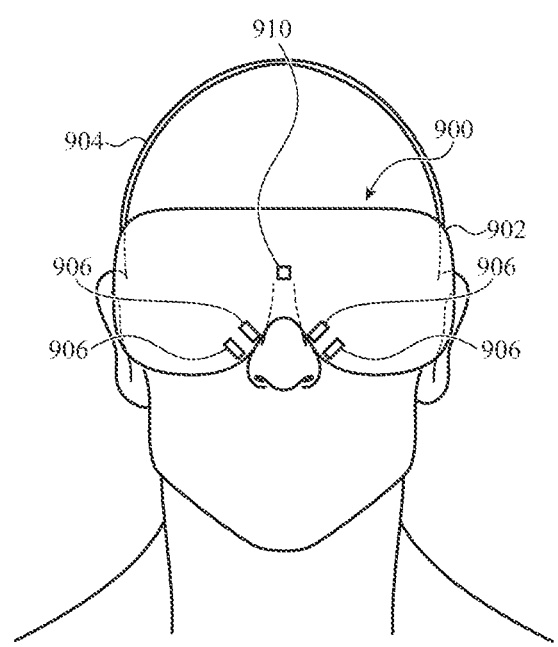

FIG. 11 shows a front view of the wearable device 900 being worn by the user according to one embodiment of the present disclosure. As shown, the wearable device 900 may include interferometric sensors 906 distributed in a symmetrical fashion about the nose of the user. The reference sensor 910 is also shown.

Figure 12:
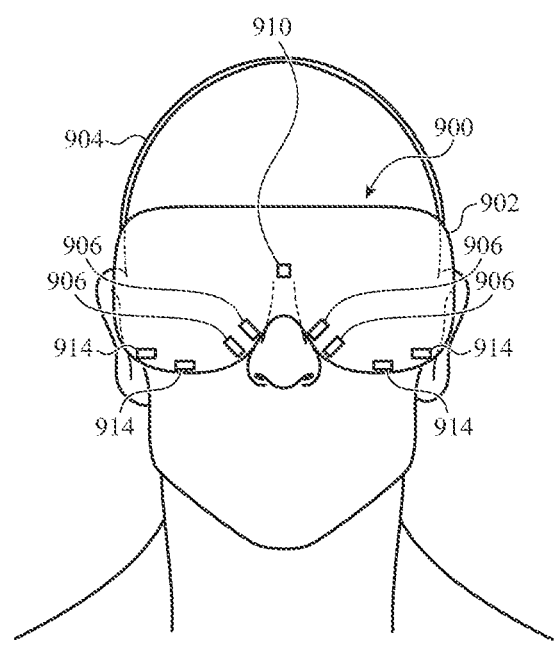

FIG. 12 shows a front view of the wearable device 900 being worn by the user according to an additional embodiment of the present disclosure. The wearable device 900 shown in FIG. 12 is similar to that shown in FIG. 11, but further includes a number of electromagnetic radiation detectors 914 distributed throughout the housing 902. As discussed herein, the electromagnetic radiation detectors 914 may sense off-axis reflections and/or backscatter of electromagnetic radiation emitted from the interferometric sensors 906 to enable scatterometry and thus particle size detection.

Notably, the particular number and arrangement of interferometric sensors 906, reference sensors 910, and electromagnetic radiation detectors 914 shown in FIGS. 9-12 are for purposes of illustration only, and are not meant to be exhaustive or limiting. In general, the wearable device 900 may include any number of interferometric sensors 906, reference sensors 910, and/or electromagnetic radiation detectors 914 positioned and oriented in the housing in any configuration without departing from the principles of the present disclosure.

Further, the form factor of the wearable device 900 shown in FIGS. 9-12 is meant to be illustrative and not exhaustive. The principles described herein, including positioning and orienting interferometric sensors in the housing of a wearable device to detect particle movement from respiration of a user and the subsequent applications thereof, may be applied to wearable devices have any suitable form factor (e.g., eyewear, face masks, goggles, safety glasses, or the like).

Figure 13A:
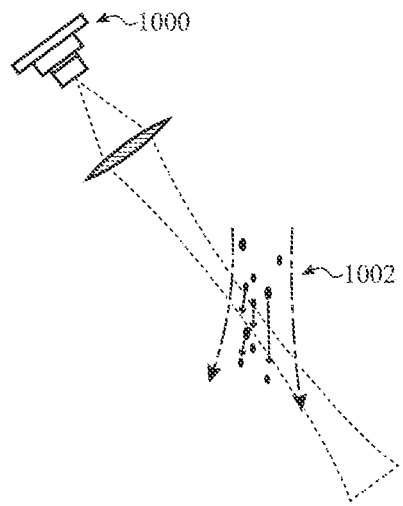
FIGS. 13A through 13C show various configurations for interferometric sensors, such as described herein.
Figure 13B:
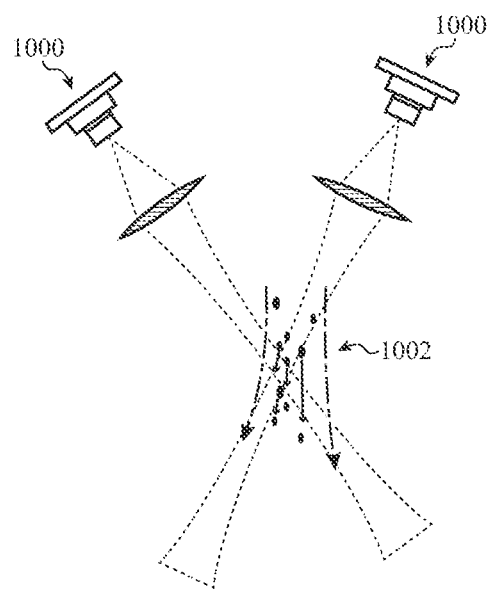
Figure 13C:
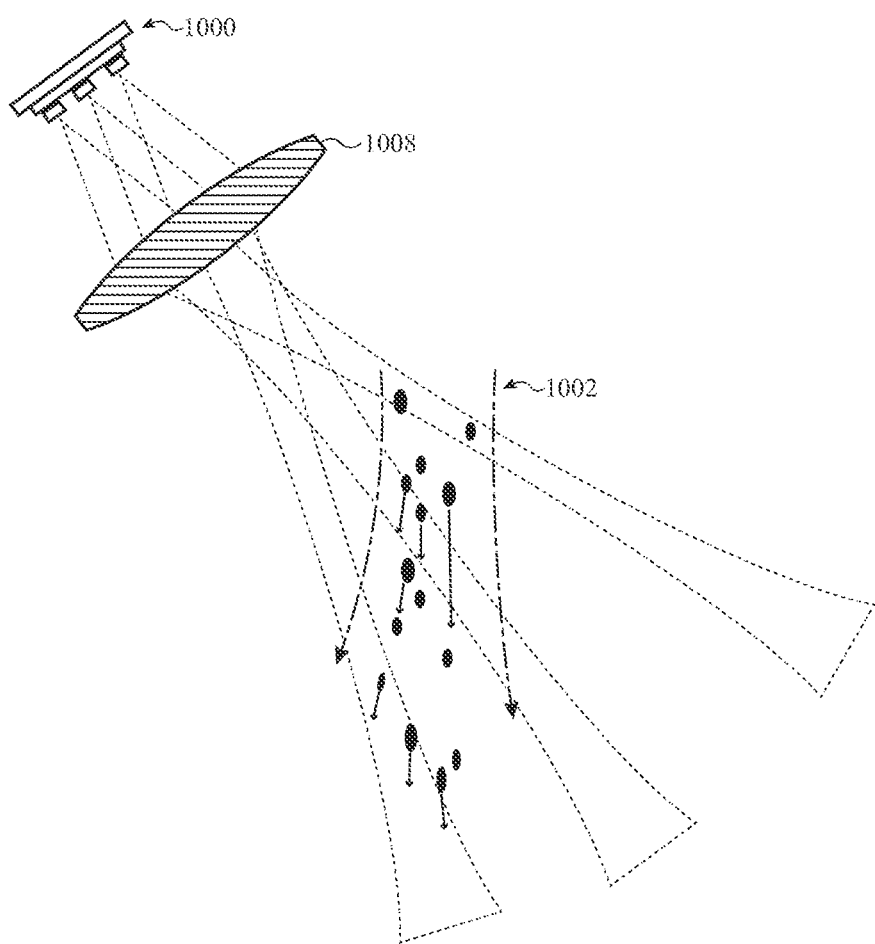

In some aspects, it may be useful to position and orient interferometric sensors so that the electromagnetic radiation emitted therefrom partially or completely overlaps within a desired area. This may improve accuracy and/or reliability of measurements. FIGS. 13A through 13C illustrate a number of exemplary configurations for interferometric sensors 1000 with respect to an area 1002 experiencing airflow due to respiration of a user. FIG. 13A shows a single interferometric sensor 1000 emitting electromagnetic radiation towards the area 1002. FIG. 13B shows two interferometric sensors 1000 that are not co-planar emitting electromagnetic radiation such that the electromagnetic radiation overlaps within the area 1002. FIG. 13C shows three interferometric sensors 1000 that are co-planar emitting electromagnetic radiation that does not overlap within the area 1002. As shown, an optic 1004 may be used to achieve this configuration. Notably, the configurations shown in FIGS. 13A through 13C are merely illustrative, and not exhaustive. In general, any number of interferometric sensors may be positioned and oriented to overlap the electromagnetic radiation emitted therefrom within an area of interest, or not, in order to achieve a desired effect.

Figure 14:
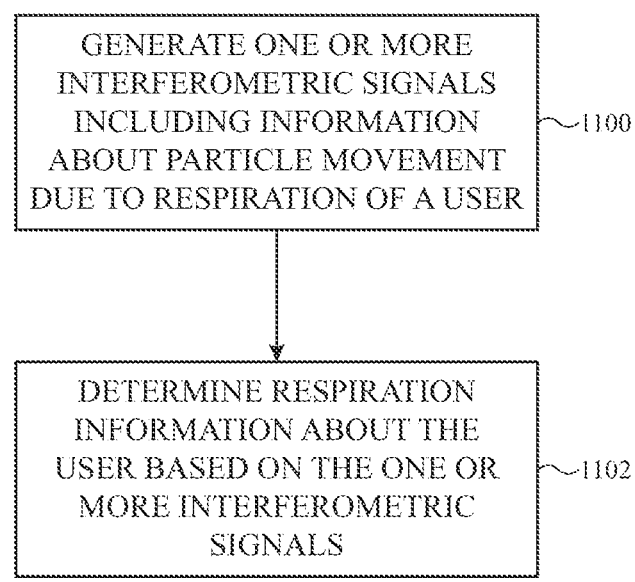
FIG. 14 is a flow diagram illustrating a method of operating a wearable device, such as described herein.

FIG. 14 is a flow diagram illustrating a method of operating a wearable device according to one aspect of the present disclosure. A set of one or more interferometric signals is generated by one or more interferometric sensors in the wearable device (step 1100). The one or more interferometric signals may include information about particle movement due to respiration of the user. For example, the one or more interferometric signals may include information about particle movement due to inhalation and/or exhalation through the mouth and/or nose of the user. Accordingly, the one or more interferometric sensors may be positioned and oriented in a housing of the wearable device to emit electromagnetic radiation towards an expected airflow path for respiration of the user, for example, in front of the nose and/or mouth of the user.

Next, respiration information about the user is determined based on the one or more interferometric signals (step 1102). The respiration information may be determined, for example, by providing the one or more interferometric signals to a machine learning model. In general, any suitable calculation, transformation, estimation, or the like may be performed on the interferometric signals to determine the respiration information therefrom. The respiration information may include one or more of respiration rate, respiration velocity, respiration volume, respiration quality, whether a user is breathing through a nose or a mouth, information about particles inhaled, and information about particles exhaled. In some aspects, the respiration information may be displayed graphically for the user. The wearable device may use the respiration information to notify the user of certain events, such as when the user is experiencing a particular level of nasal congestion (which may be indicative of seasonal allergies and/or illness), when the user is breathing through the mouth rather than the nose, etc. Further, visualizations of the user's breathing may be generated and shown to the user, which may aid in activities such as guided breathing or biofeedback. In some aspects, the user's breathing may be used as an input for an application, such as for blowing out candles in a video game. The user's breathing may also be used to generate feedback for a user in any suitable fashion, such as haptic feedback, audio alerts, visual alerts, or the like. If it is detected that a user stops breathing, emergency services can be contacted to provide medical aid, in some cases automatically. The principles of operation described with respect to FIG. 14 may be used in any of the wearable devices described herein.

Information from interferometric sensors discussed herein may be used along with complimentary data streams from other sensors (which may be located on other devices) to obtain or discern additional information about a user or unlock additional applications. For example, data from a wrist-worn device worn by the user may be combined with data from the interferometric sensors discussed herein to obtain additional information about the user. Further, data from a non-wearable device, such as a device in the environment around the user, may be combined with data from the interferometric sensors discussed herein to obtain additional information about the user. Data from a wearable device worn by a different user may also be combined with data from interferometric sensors worn in a wearable device as described herein to enable additional functionality (e.g., improved gaming experiences between users). In one example, blood oxygen saturation information from a blood oxygen saturation sensor in a wearable device worn by the user may be combined with respiration information obtained as discussed herein. The blood oxygen saturation information may enrich the respiration information to enable discernment of respiration events such as a user holding their breath versus a user choking or drowning. Gaze tracking information may be combined with respiration information to determine information about a user such as attentiveness and focus on a task (e.g., student or driver focus), which may enable a user to be notified to take a break as attentiveness wanes. Respiration information, alone or combined with other information about a user, may enable a wearable device to provide breathing queues (e.g., when to breathe in, when to hold breath, when to breathe out, and breathing pacing), either for general health or related to a particular task such as for improving performance in sporting or other activities (e.g., swimming, diving, golf, tennis, archery, and baseball).

Respiration information, along with other complimentary information, may also be used to track a user's breathing or health trends over time. Such information may be indicative of training capacity and whether a particular training regimen is effective for a user. Respiration information, along with other complimentary information, may also provide an unobtrusive way to monitor an emotional response of a user, for example, by detecting gasping, laughter, crying, sobbing, speech and speech emphasis, etc. Monitoring emotional response via respiration information may be less obtrusive than directly monitoring audio. Emotional response information may in turn be useful in determining a user's response to various environmental stimuli or medications, which a user may wish to track over time.

Figure 15:
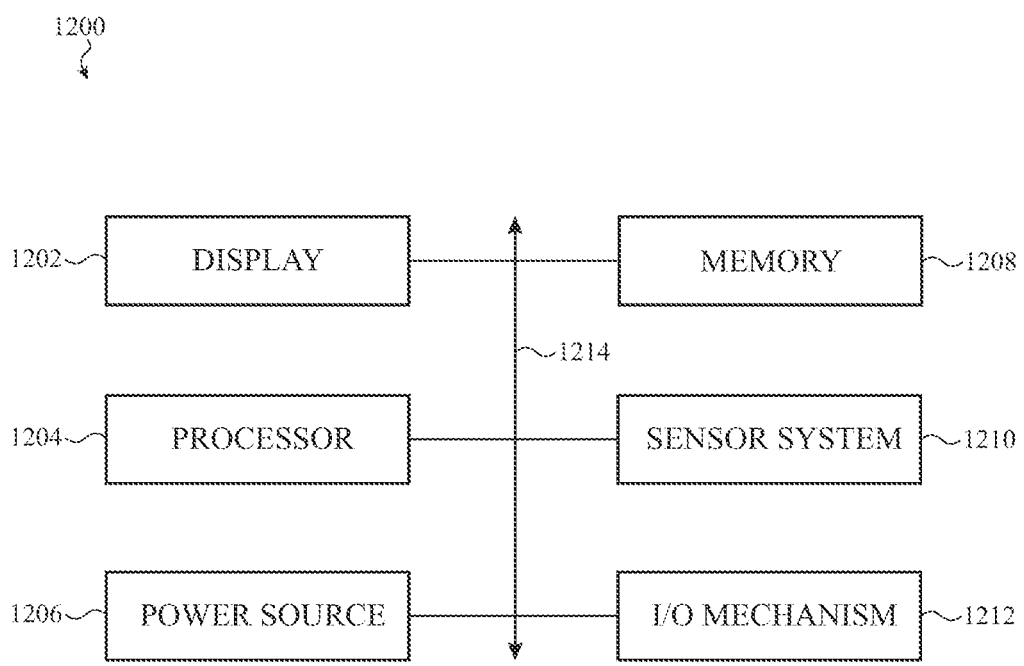
FIG. 15 is an example electrical block diagram of a wearable device, such as described herein.

FIG. 15 shows a sample electrical block diagram of a wearable device 1200, which may be implemented as any of the devices described with respect to FIGS. 1, 3-5B, and 8-12. The wearable device 1200 may include an electronic display 1202 (e.g., a light-emitting display), a processor 1204 (also referred to herein as processing circuitry), a power source 1206, a memory 1208, or storage device, a sensor system 1210, an input/output (I/O) mechanism 1212 (e.g., an input/output device, input/output port, or haptic input/output interface). The processor 1204 may control some or all of the operations of the wearable device 1200. The processor 1204 may communicate, either directly or indirectly, with some or all of the other components of the wearable device 1200. For example, a system bus or other communication mechanism 1214 can provide communication between the electronic display 1202, the processor 1204, the power source 1206, the memory 1208, the sensor system 1210, and the I/O mechanism 1212.

The processor 1204 may be implemented as any electronic device capable of processing, receiving, or transmitting data or instructions, whether such data or instructions is in the form of software or firmware or otherwise encoded. For example, the processor 1204 may include a microprocessor, central processing unit (CPU), an application-specific integrated circuit (ASIC), a digital signal processor (DSP), a controller, or a combination of such devices. As described herein, the term "processor" or "processing circuitry" is meant to encompass a single processing unit, multiple processors, multiple processing units, or other suitably configured computing element or elements. In some embodiments, the processor 1204 may provide part or all of the processing systems, processing circuitry, or processors described with reference to any of FIGS. 1, 3-5B, and 8-12.

It should be noted that the components of the wearable device 1200 can be controlled by multiple processors. For example, select components of the wearable device 1200 (e.g., the sensor system 1210) may be controlled by a first processor and other components of the wearable device 1200 (e.g., the electronic display 1202) may be controlled by a second processor, where the first and second processors may or may not be in communication with each other.

The power source 1206 can be implemented with any device capable of providing energy to the wearable device 1200. For example, the power source 1206 may include one or more batteries or rechargeable batteries. Additionally or alternatively, the power source 1206 may include a power connector or power cord that connects the wearable device 1200 to another power source, such as a wall outlet.

The memory 1208 may store electronic data that can be used by the wearable device 1200. For example, the memory 1208 may store electrical data or content such as, for example, audio and video files, documents and applications, device settings and user preferences, timing signals, control signals, and data structures and databases. The memory 1208 may include any type of memory. By way of example only, the memory 1208 may include random access memory (RAM), read-only memory (ROM), flash memory, removeable memory, other types of storage elements, or combinations of such memory types.

The wearable device 1200 may also include one or more sensor systems 1210 positioned almost anywhere on the wearable device 1200. For example, the sensor system 1210 may include any and all of the sensors discussed herein with respect to FIGS. 1, 3-5B, and 8-12. The sensor system 1210 may be configured to sense one or more types of parameters, such as but not limited to: vibration, light, touch, force, heat, movement, relative motion, biometric data (e.g., biological parameters) of a user, air quality, proximity, position, or connectedness. By way of example, the sensor system 1210 may include one or more interferometric sensors as discussed herein with respect to FIGS. 1, 3-5B, and 8-12, a heat sensor, a position sensor, a light or optical sensor, an accelerometer, a pressure transducer, a gyroscope, a magnetometer, a health monitoring sensor, and/or an air quality sensor. Additionally, the one or more sensor systems 1210 may utilize any suitable sensing technology, including, but not limited to, interferometric, magnetic, capacitive, ultrasonic, resistive, optical, acoustic, piezoelectric, or thermal technologies.

The I/O mechanism 1212 may transmit or receive data from a user or another electronic device. The I/O mechanism 1212 may include the electronic display 1202, a touch sensing input surface, a crown, one or more buttons (e.g., a graphical user interface "home" button), one or more cameras (including an under-display camera), one or more microphones or speakers, one or more ports such as a microphone port, and/or a keyboard. Additionally or alternatively, the I/O mechanism 1212 may transmit electronic signals via a communications interface, such as a wireless, wired, and/or optical communications interface. Examples of wireless and wired communications interfaces include, but are not limited to, cellular and Wi-Fi communications interfaces.

The foregoing description, for purposes of explanation, uses specific nomenclature to provide a thorough understanding of the described embodiments. However, it will be apparent to one skilled in the art, after reading this description, that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art, after reading this description, that many modifications and variations are possible in view of the teachings herein.

As described herein, one aspect of the present technology may be the gathering and use of data available from various sources, including biometric data (e.g., information about a person's respiration and movement). The present disclosure contemplates that, in some instances, this gathered data may include personal information data that uniquely identifies or can be used to identify, locate, or contact a specific person. Such personal information data can include, for example, biometric data and data linked thereto (e.g., demographic data, location-based data, telephone numbers, email addresses, home addresses, data or records relating to a user's health or level of fitness (e.g., vital signs measurements, medication information, exercise information), date of birth, or any other identifying or personal information).

The present disclosure recognizes that the use of such personal information data, in the present technology, can be used to the benefit of users. For example, the personal information data can be used to authenticate a user to access their device, or gather performance metrics for the user's interaction with an augmented or virtual world. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide data to targeted content delivery services. In yet another example, users can select to limit the length of time data is maintained or entirely prohibit the development of a baseline profile for the user. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other nonpersonal information available to the content delivery services, or publicly available information.

What is claimed is:

1. A head mounted device, comprising:
   a housing;
   one or more interferometric sensors disposed in the housing, each of the one or more interferometric sensors configured to:
      emit electromagnetic radiation towards an expected airflow path for respiration of a user; and
      generate one or more interferometric signals including information about particle movement in the expected airflow path for respiration of the user, wherein:
   the one or more interferometric sensors comprise a first interferometric sensor and a second interferometric sensor; and
   the first interferometric sensor includes one or more of a focal length, a depth of field, a numerical aperture, an angle of incidence with respect to a plane located in the expected airflow path for respiration of the user, and one or more characteristics of the electromagnetic radiation emitted therefrom that is different from the second interferometric sensor.

2. The head mounted device of claim 1, further comprising processing circuitry communicably coupled to the one or more interferometric sensors and configured to determine respiration information about the user using the one or more interferometric signals.

3. The head mounted device of claim 2, wherein the respiration information includes one or more of:
   respiration rate;
   respiration velocity;
   respiration volume;
   respiration quality;
   whether a user is breathing through a nose or a mouth;
   information about particles inhaled; or
   information about particles exhaled.

4. The head mounted device of claim 1, wherein the one or more interferometric sensors include self-mixing interferometric (SMI) sensors.

5. The head mounted device of claim 1, wherein the one or more interferometric sensors include Mach-Zender interferometric (MZI) sensors.

6. The head mounted device of claim 1, further comprising one or more reference interferometric sensors, the one or more reference interferometric sensors configured to:
   emit electromagnetic radiation towards an area outside the expected airflow path for respiration of the user; and
   generate one or more reference interferometric signals including information about particle movement in the area outside the expected airflow path for respiration of the user.

7. The head mounted device of claim 6, wherein the processing circuitry is communicably coupled to the one or more reference interferometric sensors and configured to determine the respiration information about the user based on the one or more interferometric signals and the one or more reference interferometric signals.

8. The head mounted device of claim 1, further comprising a display disposed in the housing.

9. The head mounted device of claim 8, wherein the processing circuitry is communicably coupled to the display and configured to cause the display to change in response to respiration of the user.

10. A method of operating a head mounted device, comprising:
    generating, from a set of one or more interferometric sensors disposed in a housing of the head mounted device, one or more interferometric signals including information about particle movement caused by respiration of a user;
    determining, by processing circuitry in the head mounted device, respiration information about the user based on the one or more interferometric signals; and
    generating, from a set of one or more reference interferometric sensors in the housing of the head mounted device, one or more reference interferometric signals including information about particle movement that is not caused by respiration of the user.

11. The method of claim 10, wherein the respiration information about the user includes one or more of:
    respiration rate;
    respiration velocity;
    respiration volume;
    respiration quality;
    whether a user is breathing through a nose or a mouth;
    information about particles inhaled; and
    information about particles exhaled.

12. The method of claim 10, wherein the one or more interferometric sensors are self-mixing interferometric (SMI) sensors.

13. The method of claim 10, wherein the one or more interferometric sensors are Mach-Zender interferometric (MZI) sensors.

14. The method of claim 10, wherein the respiration information about the user is determined based on the one or more interferometric signals and the one or more reference interferometric signals.

15. A head mounted device, comprising:
    a housing;
    a first interferometric sensor disposed in the housing and configured to:
       emit first electromagnetic radiation towards a first expected airflow path for respiration of a user; and
       generate first interferometric signals including information about particle movement in the first expected airflow path for respiration of the user;
    a second interferometric sensor disposed in the housing and configured to:
       emit second electromagnetic radiation towards a second expected airflow path for respiration of the user, the second expected airflow path different from the first expected airflow path; and
       generate second interferometric signals including information about particle movement in the second expected airflow path for respiration of the user; and
    a plurality of electromagnetic radiation detectors distributed within the housing and comprising:
       first electromagnetic radiation detectors configured to generate first detector signals including information about reflections of the first electromagnetic radiation emitted from the first interferometric sensor from one or more particles in the first expected airflow path; and
       second electromagnetic radiation detectors configured to generate second detector signals including information about reflections of the second electromagnetic radiation emitted from the second interferometric sensor from one or more particles in the second expected airflow path.

16. The head mounted device of claim 15, further comprising processing circuitry communicably coupled to the first and second interferometric sensors and the first and second electromagnetic radiation detectors, the processing circuitry configured to determine a particle size of one or more particles in the first and second expected airflow paths for respiration of the user based on the first and second interferometric signals and the first and second detector signals.

17. The head mounted device of claim 16, wherein the processing circuitry is further configured to determine respiration information about the user based on the first and second interferometric signals and the first and second detector signals.

18. The head mounted device of claim 17, wherein the respiration information includes one or more of:
- respiration rate;
- respiration velocity;
- respiration volume;
- respiration quality;
- whether a user is breathing through a nose or a mouth;
- information about particles inhaled; and
- information about particles exhaled.

* * * * *